United States Patent [19]

Eriksoo et al.

[11] 4,061,747

[45] Dec. 6, 1977

[54] ANTIDEPRESSANT COMPOSITION

[75] Inventors: Edgar Eriksoo; Korfitz Bengt-Ingvar Ohlsson, both of Helsingborg, Sweden

[73] Assignee: Aktiebolaget Leo, Helsingborg, Sweden

[21] Appl. No.: 697,765

[22] Filed: June 21, 1976

[30] Foreign Application Priority Data

July 3, 1975  United Kingdom .............. 28136/75

[51] Int. Cl.$^2$ ............................................. A61K 31/33
[52] U.S. Cl. ..................................... 424/244; 424/280
[58] Field of Search ................................ 424/280, 244

[56] References Cited

FOREIGN PATENT DOCUMENTS 1,177,525   1/1970   United Kingdom.

*Primary Examiner*—Stanley J. Friedman
*Attorney, Agent, or Firm*—Gordon W. Hueschen

[57] ABSTRACT

This invention relates to novel solid compositions, e.g., tablets, pills, dispersible powders, granules, or capsules, containing as active ingredient the compound 4'-chloro-2-{[3-(10,11-dihydro-5H-dibenz(b,f)-azepinyl-(5)-propyl]-methylamino}-acetophenone hydrochloride (in the following referred to as lofepramine hydrochloride).

7 Claims, No Drawings

ANTIDEPRESSANT COMPOSITION

The present invention relates to novel solid compositions, e.g., tablets, pills, dispersible powders, granules, or capsules, containing as active ingredient the compound 4'-chloro-2-{[3-(10,11-dihydro-5H-dibenz(b,f)-azepinyl-(5))-propyl]-methylamino}-acetophenone hydrochloride (in the following referred to as lofepramine hydrochloride). This compound is known, e.g., from the British Pat. No. 1,177,525, and has been found clinically effective against disorders related to the central nervous system, especially mental depressions (B. Siwers et al., Europ. J. Clin. Pharmacol. 3 (1970) 12–17).

Example 8 of the above-mentioned British Pat. No. 1,177,525 shows a conventional formulation of a composition containing lofepramine in tablets.

It has, however, been found that said compound decomposes in this and similar conventional formulations. Among the decomposition products, such compounds as N-formyl-N-methyl-3-(10,11-dihydro-5H-dibenz(b,f)azepin-5-yl)-propylamine and 4-chlorobenzoic acid have been found. It has, however, been impossible to determine the exact nature of this decomposition.

As the compound is used orally, it is important to prevent such decomposition. Sugar coating or film coating of the tablets has been found incapable of preventing decomposition of the compound. Neither has it been possible to obtain a stabilization effect by using acceptable amounts of a suitable additive which is a standard antioxidant and which is itself stable in contact with the active ingredient, i.e., ethylgallate. Results from such experiments are shown in Table 1 below.

Because of the foregoing considerations, the nature of the decomposition remains unresolved.

It has, however, now unexpectedly been found that solid compositions having considerably improved stability with regard to lofepramine can be prepared if a stabilizing amount of ascorbic acid is added to the composition in question. The amount of ascorbic acid necessary to reduce the decomposition of lofepramine in such solid compositions is preferably at least three per cent by weight of the composition. Furthermore, it is generally preferred to include in the composition an amount of ascorbic acid which is not more than about 50 percent by weight of the composition, although this upper limit is in no way critical.

In addition to the active ingredient and the stabilizing amount of ascorbic acid, the composition may contain the usual pharmaceutically acceptable carriers, diluents, or excipients, as well as other conventional ingredients in such type of formulations, such as binders, lubricants, preservatives, etc. In addition, the compositions may contain other active ingredients having the same or other indication as the active ingredient of the invention first above-identified.

Such solid compositions for oral administration include compressed tablets, pills, dispersible powders, granules or capsules. In such solid compositions the active compound, in addition to ascorbic acid, is admixed with at least one inert diluent such as a starch of any of various different origins, alginic acid, lactose, calcium carbonate, calcium phosphate, calcium sulphate, dextrose, mannitol and celluloses of different types and origins. The compositions may also comprise, as is normal practice, additional inert substances other than diluents e.g., lubricating agents, such as magnesium stearate, Pruv ® (sodium stearyl fumarate), Sterotex ® (edible vegetable oil product), talc and binding agents, such as gelatine, polyvinylpyrrolidone, methylcellulose, hydroxypropylcellulose, polyethyleneglycols, etc. Besides inert diluents, the compositions may also comprise adjuvants, such as wetting and suspending agents, and sweetening, flavouring, and preserving agents.

The percentage of active ingredient in the composition of the invention may be varied, it being necessary only that it should constitute a proportion such that a suitable orally-effective dosage for the therapeutic effect desired shall be obtained. In general, the compositions for oral administration will normally contain at least ten percent by weight of active substances, although higher and lower percentages are operative. The dose employed depends upon the desired therapeutic effect, and the duration of the treatment. In an adult, the doses are generally between fifty and 300 mg per day. Orally-effective unit doses are generally between about ten and about 150 mg, usually 25 to 50 mg.

In order to illustrate this invention, the following examples are given by way of illustration only and not by way of limitation.

Example 1
(wet granulation technique). For 1000 tablets.

| | | |
|---|---|---|
| I | Lofepramine HCl, sieve No. 20 (mesh 50 ASTM E 11-61) corresponding to lofepramine (as base) 35 mg each per tablet | 38.05 g |
| | Lactose | 82.0 g |
| | Corn starch | 61.5 g |
| | Ascorbic acid | 5.0 g |
| II | Gelatine | 4.0 g |
| | Glycerine | 1.65 g |
| | Distilled water q.s. about | 28 g |
| III | Disodium edetate | 0.25 g |
| | Ascorbic acid | 5.0 g |
| IV | Ascorbic acid, sieve No. 20 (mesh 50) | 15.0 g |
| | Corn starch | 20.0 g |
| | Sterotex regular (Capital City Products Co.) (edible vegetable oil product), sieve No. 10 (mesh 25) | 1.5 g |
| | Talc q.s. ad | 250.0 g |
| | Weight of 1000 tablets: | 250.0 g |
| | Weight of 1 tablet: | 250 g |

A mixture of I is moistured with a freshly-prepared solution of II + III at a temperature not exceeding 40° C and granulated through a 1.6 mm screen, dried at room temperature, and then passed through a 1.5 mm screen. The resulting granulation (G) is mixed with the mixture IV and finally compressed into tablets. Alternatively, the resulting granulation (G) may be filled into bottles and used as such, or filled into any of a large number of types of capsules and dispensed as encapsulated granules. When an internal and an external phase are employed, as in Example 1, the internal phase contains the lofepramine hydrochloride and at least 20%, preferably about 40%, and at most about 60% of the total amount of ascorbic acid employed as stabilizing agent. Other wet granulation technique may also be employed, but a two-phase system, as illustrated by Example 1, is preferred.

The tablets are subjected to stability studies in comparison with identical tablets not containing the stabilizing amount of ascorbic acid, according to standard procedure. These stability studies show that the stabilized composition of the present invention undergoes less decomposition than the unstabilized form of the tablet, the improvement being on the order of at least 300%, the figures compared being those obtained on the two forms of the product when subjected to identical accelerated aging conditions for identical periods.

Example 2

(direct compression technique). For 1000 tablets.

| | |
|---|---|
| Lofepramine HCl, sieve No. 20 (mesh 50 ASTM E 11-61), corresponding to lofepramine (as base) 35 mg each per tablet | 38.05 g |
| Disodium edetate, sieve No. 30 (mesh 75 ASTM E 11-61) (Tetracemin dinatrium) | 0.25 g |
| Aerosil (Degussa) (Brand of colloidal silicon dioxide) | 0.25 g |
| Sterotex ® regular, sieve No. 10 (mesh 25 ASTM E 11-61) (Edible vegetable oil product) | 2.5 g |
| Ascorbic acid, sieve No. 20 (mesh 50 ASTM E 11-61). | 25.0 g |
| Lactose | 58.0 g |
| Avicel (microcrystalline cellulose) (FMC-Corp. USA) | 58.0 g |
| STaRx 1500 (STaley Manuf. Co.) (Modified corn starch) | 58.0 g |
| Talc q.s. ad | 250.0 g |
| Weight of 1000 tablets: | 250.0 g |
| Weight of 1 tablet: | 250 mg |

The substances are thoroughly granulated and admixed (sieve No. 10, mesh 25) and then the powder (P) is directly compressed into tablets.

The tablets are subjected to stability studies in comparison with identical tablets not containing the stabilizing amount of ascorbic acid, according to standard procedure. These stability studies show that the stabilized composition of the present invention undergoes less decomposition than the unstabilized form of the tablet, the improvement being on the order of at least 300%, the figures compared being those obtained on the two forms of the product when subjected to identical accelerated aging conditions for identical periods.

Alternatively, the dried powder (P) may be formed into tablets which are enteric or normally coated, or compounded into the form of sustained release granules or tablets, or rendered more readily dispersible in the usual manner, as by micronizing, or filled into capsules, or formed into pills, all according to standard pharmaceutical procedure.

EXAMPLE 3

Example 1 is repeated but using, instead of a total amount of 25.0 g of ascorbic acid, a total amount of 10.0 g of ascorbic acid, having 6.0 g in the internal phase. The same useful result is obtained with regard to tablet stability.

EXAMPLE 4

Example 1 is repeated but using, instead of a total amount of 25.0 g of ascorbic acid, a total amount of 50.0 g ascorbic acid, having 20 g in the internal phase. The same useful result is obtained with regard to tablet stability.

EXAMPLE 5

Other compositions.

In the same manner as given in the preceding examples, additional compositions containing effective amounts of the active ingredient and according to the present invention are formulated and found to be characterized by enhanced stability when compared with conventional formulations not containing a stabilizing amount of ascorbic acid, whether in bulk or in unit dosage form.

The stabilization effect of ascorbic acid is illustrated in Table 2 below.

Representative compositions characterized by this improved stability and containing a stabilizing amount of ascorbic acid according to the invention thus include: conventionally coated tablets, sustained-release granules, capsules and tablets; enteric coated tablets, as well as conventional tablets, pills, dispersible powders, granules, and capsules.

It is to be understood that the invention is not limited to the exact details of operation or exact compounds or compositions shown and described, as obvious modifications and equivalents will be apparent to one skilled in the art, and the invention is therefore to be limited only by the scope of the appended claims.

Tables 1 and 2 are found on the following pages, 9 and 10, respectively.

Table 1

| Tablets prepared according to | Tablet weight mg | Amount lofepramine hydrochloride in a tablet mg | Means of stabilization | | Storage conditions | | Loss of lofepramine hydrochloride % |
|---|---|---|---|---|---|---|---|
| | | | Film-coated | Stabilization agent | Time in months | Temp. °C | |
| Ex. 1 | 250 | 26.18 1) | Yes | None | 20 | 20 | 21.6 |
| " | 250 | 38.05 2) | No | Ascorbic acid | 26 | 20 | 1.7 |
| " | 250 | 38.05 | No | Ethyl gallate | 26 | 20 | 19.7 3) |

1) This amount corresponds to 25 mg of lofepramine base.
2) This amount corresponds to 35 mg of lofepramine base.
3) This experiment shows that the decomposition of lofepramine hydrochloride is not a simple oxidation problem.

Table 2

| Tablets prepared According to | Tablet weight mg | Amount lofepramine hydrochloride in tablet mg | Amount ascorbic acid in a tablet mg | Storage Conditions | | Loss of lofepramine hydrochloride % |
|---|---|---|---|---|---|---|
| | | | | Time in months | Temp. °C | |
| Ex. 1 1) | 250 | 38.05 5) | 0 | 8 | 37 | 27.4 |
| " | 250 | 38.05 | 25 4) | 8 | 37 | 4.6 |
| Ex. 8 2) | 285 | 54.35 6) | 0 | 8 | 37 | 22.4 |
| " | 3) | 285 | 54.35 | 35.7 4) | 8 | 37 |

1) The amount of ascorbic acid is here replaced by lactose.
2) Found in the British Patent No. 1,177,525.
3) The amount of lactose is reduced to 1243 g to permit inclusion of ascorbic acid.
4) This amount is 65.7 % of the amount of lofepramine hydrochloride.
5) This amount corresponds to 35 mg of lofepramine base.
6) This amount corresponds to 50 mg of lofepramine base.

We claim:

1. Solid antidepressant composition for oral use containing as active ingredient an orally-effective amount of lofepramine hydrochloride, at least ten percent by weight of the composition, a pharmaceutically-acceptable carrier, and a stabilizing amount, at least three percent by weight of the composition, of ascorbic acid.

2. Composition of claim 1 in the form of a granulated material.

3. Composition of claim 2, wherein said granulated material has an internal and an external phase and wherein the internal phase contains the lofepramine hydrochloride and up to about sixty percent of the total amount of ascorbic acid present in the composition.

4. Composition of claim 3 in the form of a tablet.

5. Method for the preparation of a composition of claim 1, which comprises admixing the ingredients and forming them into the form of a solid antidepressant composition having improved stability characteristics.

6. Method of claim 5, wherein the ingredients are mixed together in two separate admixtures, the first mixture containing the lofepramine hydrochloride and up to about 60 percent of the total amount of ascorbic acid present in the composition, said first mixture is wet granulated and then mixed with the second mixture of ingredients to produce a granulated material having an internal and an external phase, wherein said internal phase contains said first mixture of ingredients.

7. Method of claim 6, wherein said granulation is compressed into the form of a tablet.

* * * * *

UNITED STATES PATENT OFFICE
CERTIFICATE OF CORRECTION

Patent No. 4,061,747        Dated Dec. 6, 1977

Inventor(s) Edgar Eriksoo et al

It is certified that error appears in the above-identified patent and that said Letters Patent are hereby corrected as shown below:

Col. 2, line 39, "Sterotex regular" should read
-- Sterotex® regular--
Col. 4, line 41-42; "Tables 1 and 2 are found on the following pages,9 and 10, respectively." should read --Tables 1 and 2 are found below.--
Col. 4, line 63; The last line of Table 2 should be moved over one column.
Col. 4, line 63; The last column on the far right "4" should read --4.8--.

Signed and Sealed this

Twenty-eighth Day of March 1978

[SEAL]

Attest:

RUTH C. MASON
*Attesting Officer*

LUTRELLE F. PARKER
*Acting Commissioner of Patents and Trademarks*